(12) United States Patent
Koseoglu et al.

(10) Patent No.: US 10,401,344 B2
(45) Date of Patent: Sep. 3, 2019

(54) CHARACTERIZATION OF CRUDE OIL AND ITS FRACTIONS BY THERMOGRAVIMETRIC ANALYSIS

(71) Applicant: Saudi Arabian Oil Company, Dhahran (SA)

(72) Inventors: Omer Refa Koseoglu, Dhahran (SA); Adnan Al-Hajji, Dhahran (SA); Amer A. Al-Tuwailib, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 712 days.

(21) Appl. No.: 14/987,834

(22) Filed: Jan. 5, 2016

(65) Prior Publication Data

US 2016/0195481 A1 Jul. 7, 2016

Related U.S. Application Data

(60) Provisional application No. 62/099,623, filed on Jan. 5, 2015.

(51) Int. Cl.
*G01N 25/48* (2006.01)
*G01N 33/28* (2006.01)
*G01N 33/30* (2006.01)

(52) U.S. Cl.
CPC ......... *G01N 33/30* (2013.01); *G01N 25/4833* (2013.01); *G01N 33/2811* (2013.01); *G01N 33/2823* (2013.01)

(58) Field of Classification Search
CPC ........ G01N 25/00; G01N 33/28; G01N 33/24; G01N 33/30

USPC ..................................................... 374/14, 45
See application file for complete search history.

(56) References Cited

U.S. PATENT DOCUMENTS

| | | | |
|---|---|---|---|
| 3,617,501 | A | 11/1971 | Eng |
| 3,896,312 | A | 7/1975 | Brown |
| 4,251,870 | A | 2/1981 | Jaffe |
| 4,897,177 | A | 1/1990 | Nadler |
| 4,971,915 | A | 11/1990 | Schwartz et al. |
| 4,988,446 | A | 1/1991 | Haberman |
| 5,121,337 | A | 6/1992 | Brown |
| 5,223,714 | A | 6/1993 | Maggard |
| 5,266,800 | A | 11/1993 | Mullins |

(Continued)

FOREIGN PATENT DOCUMENTS

| | | |
|---|---|---|
| CA | 2781273 A1 | 12/2013 |
| EP | 0305090 A2 | 8/1988 |

(Continued)

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.

(Continued)

*Primary Examiner* — Lisa M Caputo
*Assistant Examiner* — Janice M Soto
(74) *Attorney, Agent, or Firm* — Abelman, Frayne & Schwab

(57) ABSTRACT

A system and a method are provided for calculating the cetane number, pour point, cloud point, aniline point, aromaticity, and/or octane number of a crude oil and its fractions from the density and thermogravimetric analysis (TGA) of a sample of the crude oil.

26 Claims, 4 Drawing Sheets

(56) References Cited

U.S. PATENT DOCUMENTS

| | | |
|---|---|---|
| 5,304,807 A | 4/1994 | Lin |
| 5,424,959 A | 6/1995 | Reyes |
| 5,452,232 A | 9/1995 | Espinosa et al. |
| 5,475,612 A | 12/1995 | Espinosa |
| 5,490,085 A | 2/1996 | Lambert et al. |
| 5,572,030 A | 11/1996 | Ranson et al. |
| 5,600,134 A | 2/1997 | Ashe et al. |
| 5,602,755 A | 2/1997 | Ashe et al. |
| 5,656,810 A | 8/1997 | Alfano et al. |
| 5,699,269 A | 12/1997 | Ashe et al. |
| 5,699,270 A | 12/1997 | Ashe et al. |
| 6,070,128 A | 5/2000 | Descales |
| 6,258,987 B1 | 7/2001 | Schmidt et al. |
| 6,275,775 B1 | 8/2001 | Baco |
| 6,490,029 B1 | 12/2002 | Cho |
| 6,602,403 B1 | 8/2003 | Steffens et al. |
| 6,611,735 B1 | 8/2003 | Henly |
| 6,633,043 B2 | 10/2003 | Hegazi |
| 6,662,116 B2 | 12/2003 | Brown |
| 6,711,532 B1 | 3/2004 | Spieksma |
| 6,841,779 B1 | 1/2005 | Roehner et al. |
| 6,893,874 B2 | 5/2005 | Stark |
| 7,126,332 B2 | 10/2006 | Blanz |
| 7,173,239 B2 | 2/2007 | DiFoggio |
| 7,560,711 B2 | 7/2009 | Hegazi |
| 7,598,487 B2 | 10/2009 | Qian |
| 8,714,246 B2 | 5/2014 | Pop et al. |
| 8,930,149 B1 | 1/2015 | Koseoglu et al. |
| 9,285,307 B2 | 3/2016 | Koseoglu et al. |
| 9,423,391 B2 | 8/2016 | Koseoglu et al. |
| 9,429,556 B2 | 8/2016 | Koseoglu et al. |
| 9,778,240 B2 | 10/2017 | Koseoglu et al. |
| 9,816,919 B2 | 11/2017 | Koseoglu et al. |
| 2002/0052769 A1 | 5/2002 | Navani et al. |
| 2003/0141459 A1 | 7/2003 | Hegazi et al. |
| 2003/0195708 A1 | 10/2003 | Brown |
| 2005/0109934 A1 | 5/2005 | David |
| 2005/0173298 A1 | 8/2005 | Wellington |
| 2006/0043004 A1 | 3/2006 | Rose |
| 2006/0047444 A1 | 3/2006 | Brown |
| 2006/0142955 A1 | 6/2006 | Jones |
| 2007/0050154 A1 | 3/2007 | Albahri |
| 2007/0231912 A1 | 10/2007 | Reischman et al. |
| 2007/0295640 A1 | 12/2007 | Tan et al. |
| 2008/0037006 A1 | 2/2008 | Canas Triana |
| 2008/0040051 A1 | 2/2008 | Franklin et al. |
| 2008/0206887 A1 | 8/2008 | Chen |
| 2008/0248967 A1 | 10/2008 | Butler et al. |
| 2008/0253426 A1 | 10/2008 | Voelkening |
| 2008/0260584 A1* | 10/2008 | Gudde ............ G01N 25/08 422/69 |
| 2009/0011517 A1 | 1/2009 | Hodges |
| 2009/0180949 A1 | 7/2009 | Cui |
| 2009/0279072 A1 | 11/2009 | Arakawa |
| 2009/0290144 A1 | 11/2009 | Hegazi |
| 2009/0316139 A1 | 12/2009 | Shrestha |
| 2010/0049681 A1 | 2/2010 | Pradhan |
| 2010/0113311 A1 | 5/2010 | Eccleston et al. |
| 2010/0204925 A1 | 8/2010 | Albahri |
| 2010/0211329 A1 | 8/2010 | Farquharson et al. |
| 2010/0218585 A1 | 9/2010 | Chawla |
| 2011/0152136 A1 | 6/2011 | Hughes et al. |
| 2011/0308996 A1 | 12/2011 | Choudhary |
| 2012/0171151 A1 | 7/2012 | Thomassian |
| 2014/0075827 A1 | 3/2014 | Gonzalez et al. |
| 2014/0156241 A1 | 6/2014 | Kumar et al. |
| 2015/0106027 A1 | 4/2015 | Koseoglu et al. |
| 2015/0106028 A1 | 4/2015 | Koseoglu et al. |
| 2015/0106029 A1 | 4/2015 | Koseoglu et al. |
| 2015/0106031 A1 | 4/2015 | Koseoglu et al. |
| 2015/0112610 A1 | 4/2015 | Koseoglu |
| 2015/0112611 A1 | 4/2015 | Koseoglu |
| 2016/0003794 A1* | 1/2016 | Basu ............ G01N 33/2888 702/30 |
| 2016/0011102 A1 | 1/2016 | Koseoglu et al. |
| 2016/0187253 A1 | 6/2016 | Koseoglu et al. |
| 2016/0195481 A1 | 7/2016 | Koseoglu |
| 2016/0195507 A1 | 7/2016 | Koseoglu |
| 2016/0195508 A1 | 7/2016 | Al-Hajji |
| 2016/0377589 A1 | 12/2016 | Koseoglu |
| 2017/0003217 A1 | 1/2017 | Koseoglu |
| 2017/0363540 A1 | 12/2017 | Koseoglu |
| 2017/0363591 A1 | 12/2017 | Koseoglu |
| 2017/0363602 A1 | 12/2017 | Koseoglu |
| 2017/0363603 A1 | 12/2017 | Koseoglu |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Albahri, T. et al, Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

Bowden, J. et al., Octane-Cetane Relationship, 1974, NTIS, p. 8.

Chemstations, Inc., Physical Properties User's Guide, 2004, Chemstations Inc., Ver. 5.4, pp. 18-22.

Cookson, D.J. et al., Investigation of the Chemical Basis of Diesel Fuel Properties, Energy & Fuels, 1988, vol. 2, No. 6, pp. 854-860.

Duvekot, C., Fast Analysis of Paraffins, iso-Paraffins, Olefins, iso-Olefins, Naphthenes and Aromatics in Hydrocarbon Streams, Varian, Inc., 2008, pp. 1-4.

Evokimov, I, et al, Potential of UV-Visible Absorption Spectroscopy for characterizing Crude Petroleum Oils, Oil an Gas Business, 2007, 21 pages.

Falla, F, et al., Characterization of crude petroleum by NIR, Journal of Petroleum Science and Engineering, vol. 51, 2006, pp. 127-137.

Fernandez-Lima, F. et al., Petroleum Crude Oil Characterization by IMS-MS and FTICR MS, 2009, American Chemical Society, Ed. 81, pp. 9941-9945.

Grizzle, P. et al., Automated Liquid Chromatographic Compound Class Group-Type Separation of Crude Oils and Bitumens Using Chemically Bonded Aminoilane, 1986, Publisher Anal. Chem., vol. 58, pp. 2389-2390.

Hasan, M.U. et al., Structural characterization of Saudi Arabian heavy crude oil by n.m.r. spectroscopy, Fuel, vol. 62, 1983, pp. 518-523.

Hidajat, K, et al., Quality characterisation of crude oils by partial least square calibration of NIR spectral profiles, Near Infrared Spectrosc, vol. 8, pp. 53-59, 2000.

Jokuty, P. et al., Hydrocarbon Groups and Their Relationships to Oil Properties and Behavior, 1995, Published by Whiticar Scientific, p. 11.

Khanmohammadi, M, et al., Characterization of petroleum-based products by infrared spectroscopyu and chemometrics, Trac Trends in Analytical Chem, vol. 35, 2012.

Kok, M, et al., High pressure TGA analysis of crude oils, Thermochimica Acta., vol. 287, No. 1, 1996, pp. 91-99.

(56) References Cited

OTHER PUBLICATIONS

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.

Pande, S., et al., Cetana Number Predictions of a Trial Index Based on Compositional Analysis, American Chemical Society, 1989, pp. 308-312.

Patra, D, et al, Determination of Synchronous Fluorescence Scan Parameters for Certain Petroleum Products, Journal of Scientific & Industrial Research, Apr. 1, 2000, pp. 300-305.

Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).

Pereira,Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.

Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.

Shea, T.M., Modeling Base Oil Properties using NMR Spectroscopy and Neural Networks, Tribology Transactions, vol. 16, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Speight, Handbook of Petroleum Product Analysis, 2002.

Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.

University of Oldenburg, Institute of Physics, Catalogue of Optical Spectra of Oils, Jan. 2005, retrieved from http://las.physik.uni-oldenburg.de/data/spectra/indez.htm, 6 pages.

Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.

PCT/US2016/012108, International Search Report and Written Opinion dated May 13, 2016, 10 pages.

International Search Report and Written Opinion for related international application PCT/2016/012108, dated May 13, 2016 (10 pages).

Mustafa Versan Kok et al., "High Pressure TGA Analysis of Crude Oils," Thermochimica Acta, vol. 287, No. 1, Sep. 1, 1996, pp. 91-99.

\* cited by examiner

CHARACTERIZATION OF CRUDE OIL AND ITS FRACTIONS BY THERMOGRAVIMETRIC ANALYSIS

RELATED APPLICATION

This application claims the benefit of U.S. Provisional Patent Application No. 62/099,623 filed Jan. 5, 2015, the disclosure of which is hereby incorporated by reference.

FIELD OF THE INVENTION

This invention relates to a method and process for the evaluation of samples of crude oil and its fractions by thermogravimetric analysis (TGA).

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Micro Carbon Residue | W % | Indicative | Fraction boiling >300° C. |
| Smoke Point, mm | mm | Indicative | Fraction boiling between 150-250° C. |
| Octane Number | Unitless | Indicative | Fraction boiling <250° C. |
| Cetane Index | Unitless | Indicative | Fraction boiling between 150-400° C. |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36-180° C.), kerosene (180-240° C.), gas oil (240-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

To determine these properties of gas oil or naphtha fractions conventionally, these fractions have to be distilled from the crude oil and then measured/identified using various analytical methods that are laborious, costly and time-consuming.

Thermogravimetric Analysis (TGA) measures the changes in the materials physical and chemical properties as a function of the heating temperature. TGA is, therefore, used to determine mass loss or gain due to loss of volatiles (such as hydrocarbons and/or moisture), decomposition, or oxidation by continuously measuring the remaining weight of the sample as it losses/gains mass with heating. The result is displayed as a thermogram plot of mass versus the heating temperature. TGA has been widely used in various applications such as material characterizations, material's thermal stability, and in the determination of the sample's organic/inorganic content (such as loss-on ignition).

This invention discloses a system and method in which TGA is employed to disclose physical and indicative properties (i.e., cetane number, pour point, cloud point, and aniline point) of gas oil fraction of crude oils, as well as the octane number of the naphtha fraction and the aromaticity of whole crude oils. The invention provides insight into the gas oil properties without fractionation/distillation (crude oil assays) and will help producers, refiners, and marketers to benchmark the oil quality and, as a result, valuate the oils without going thru costly and time consuming crude oil assays. Whereas a conventional crude oil assay method could take up to two months, this invention provides results within one hour.

New rapid, and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining one or more indicative properties of a hydrocarbon sample are presented. Indicative properties in a crude oil sample (e.g., cetane number, pour point, cloud point and aniline point) of a gas oil fraction, octane number of a naptha fraction, and the aromaticity for the whole crude oil (WCO), are assigned as a function of density and thermogravimetric measurement of a crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

A system and a method are provided for determining one or more indicative properties of a hydrocarbon sample. Indicative properties (e.g., cetane number, pour point, cloud point, and aniline point) of a gas oil fraction and ozone number of a naphtha fraction in a crude oil sample are assigned as a function of the density and thermogravimetric measurement of the crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

In the system and method herein, thermogravimetric analysis is obtained by a suitable known or to-be-developed process. Thermogravimetric analysis measures a sample's weight as it is heated or cooled in a controlled atmosphere to provide volatility information of the oil sample under investigation. TGA requires a high degree of precision in the mass change and temperature. A thermogravimetric analyzer is used, comprising a furnace that contains a sample pan that is supported by a precision balance. A sample purge gas controls the sample environment. This gas may be inert or a reactive gas that flows over the sample and exits through an exhaust. In one experiment, TGA was conducted with TA Instruments (New Castle, Del.) Model #2050, equipped with the company's Universal Analyst and Thermal Advantage software. Similar equipment can be used.

The temperature range for the TGA analyzer can extend from ambient temperature (e.g., 20° C.) to an upper limit of up to 1000° C. Heating can be at a rate in the range of about 0.1-100° C./minute.

The thermogravimetric analysis index used is calculated from TGA data of a sample of whole crude oil or in certain embodiments oil well drilling cuttings. In a preferred embodiment, the thermogravimetric analysis index can be calculated at the 50 W % point of the TGA data.

In one embodiment, the thermogravimetric analysis index can be calculated by taking the average of temperature data.

In a preferred embodiment, the thermogravimetric analysis index can be calculated by taking the weighted average of temperature data.

In one embodiment, the thermogravimetric data can be obtained directly from core and/or drill cuttings material.

Figure 1:
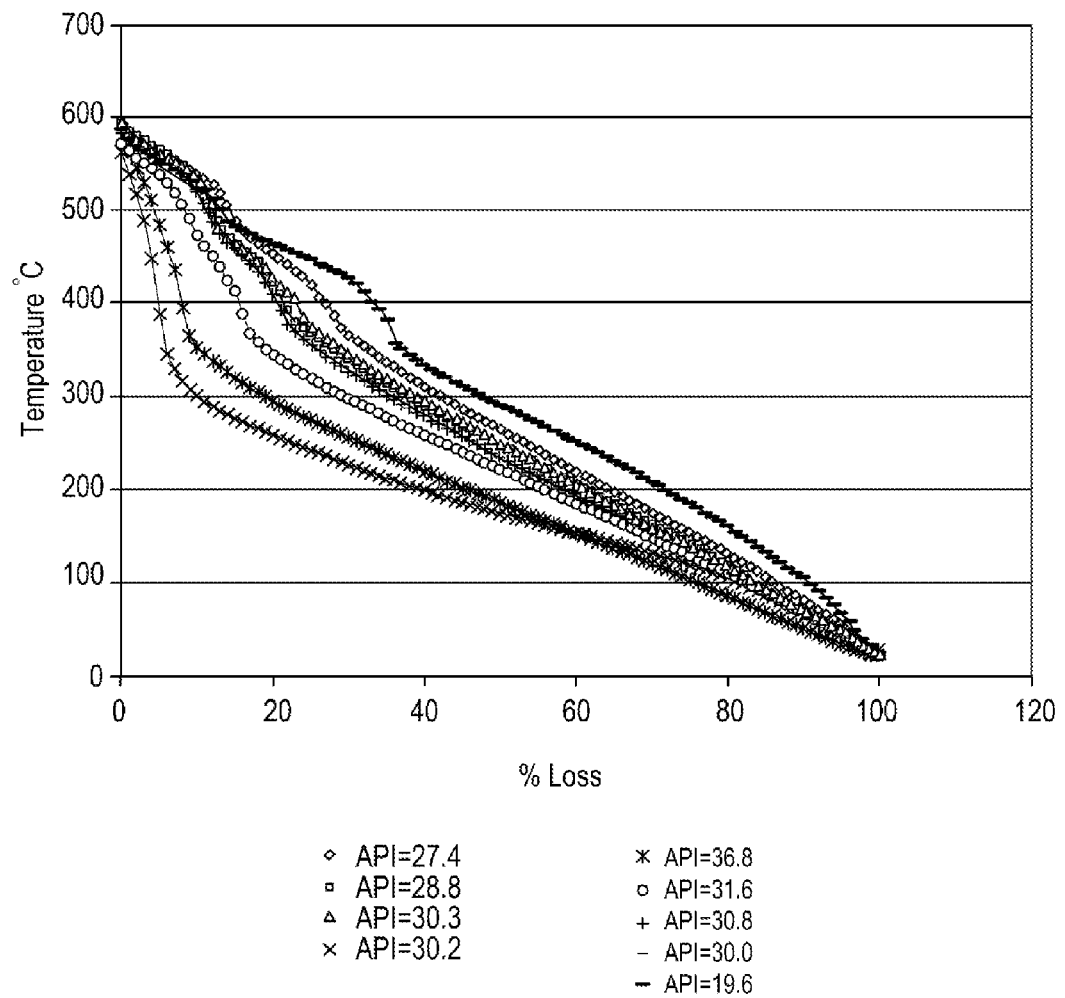
FIG. 1 is a graphic plot of typical thermogravimetric data for typical crude oil samples with different API gravities.

FIG. 1 shows a graphic plot of typical thermogravimetric data for typical crude oil samples with different API gravities.

Figure 2:
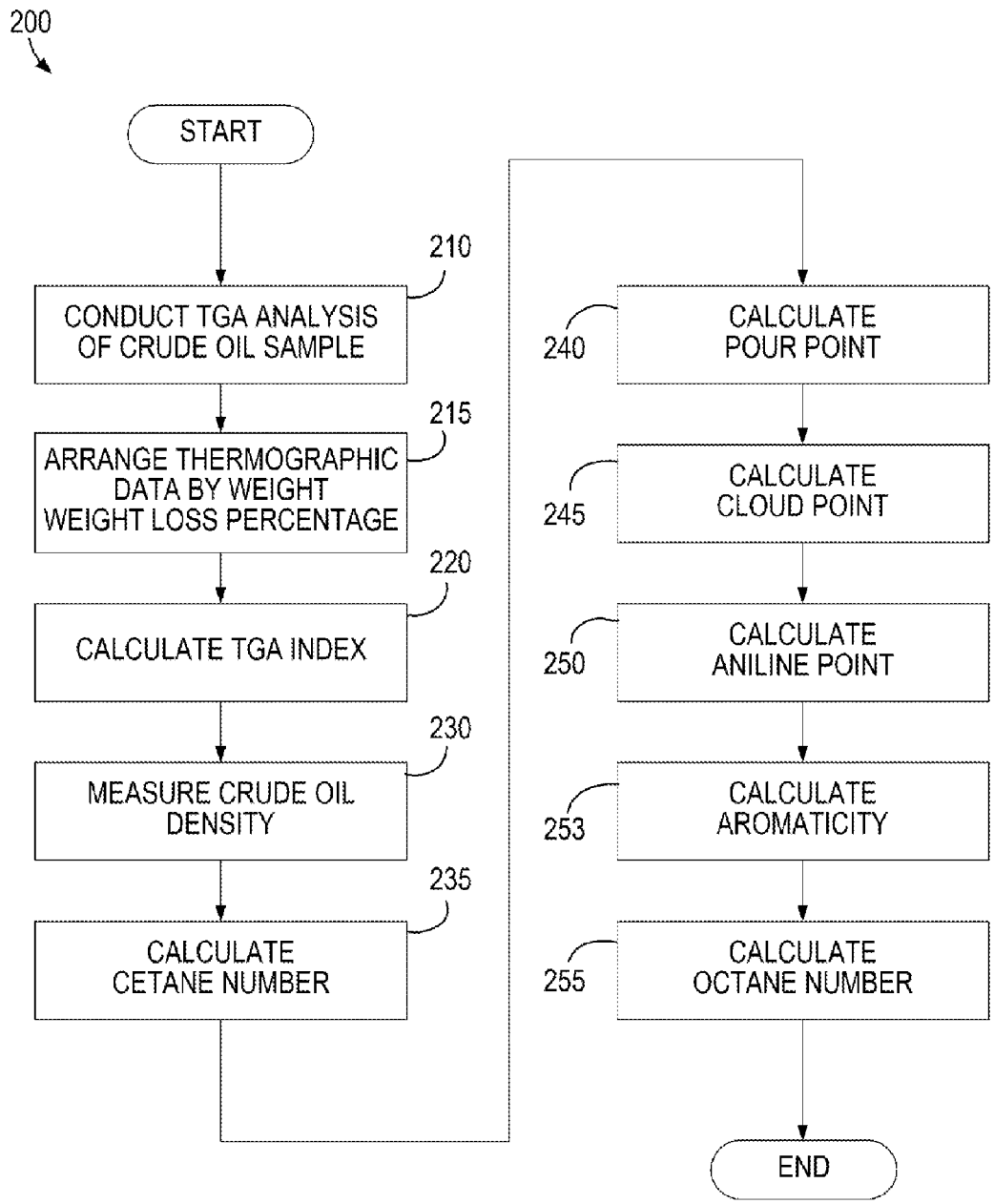
FIG. 2 is a block diagram of a method in which an embodiment of the invention is implemented.

FIG. 2 shows a process flowchart of steps in a method according to one embodiment herein, in which crude oil samples are prepared and analyzed by TGA according to the method 200 described below.

In step 210 a sample of 15-25 mg is placed via a pipette in a commercial platinum sample pan. No sample dilution or special sample preparation is required. TGA is conducted under a nitrogen atmosphere from ambient temperature to 600° C. at 10° C./minute and a gas flow of 90±5 ml/min through the furnace using calibrated rotameters. A continuous flow of nitrogen (10±1 ml/min) through the balance chamber is also maintained.

In step 215, the thermogravimetric data is arranged so that weight loss percentages (from 0 to 100) are calculated.

In step 220, a Thermogravimetric analysis index (TGAI) is calculated from the mass loss percentage and the temperature according to equation (1):

$$TGAI = \frac{\left[\begin{array}{c}5*T_5 + 10*T_{10} + 20*T_{20} + 30*T_{30} + 40*T_{40} + 50* \\ T_{50} + 60*T_{60} + 70*T_{70} + 80*T_{80} + 90*T_{90} + 95*T_{95}\end{array}\right]}{[5+10+20+30+40+50+60+70+80+90+95]}; \quad (1)$$

where $T_x$ is the temperature at individual mass loss percentage

The indicative properties (e.g., the cetane number, pour point, cloud point and aniline point) of the gas oil fraction, e.g. boiling in the range of 150-400° C. and in certain embodiments in the range of 180-370° C., the octane number of the naphtha fraction, and the aromaticity for the whole crude oil (WCO), can be assigned as a function of the density and the TGAI of crude oil. That is, $$\text{Indicative Property} = f(\text{density}_{crude\ oil}, TGAI_{crude\ oil}) \quad (2);$$

Equation (3) is a detailed example of this relationship, showing the cetane number, pour point, cloud point and aniline point that can be predicted for the gas oil (GO) fraction of the crude oil, as well as the aromaticity that can be predicted for the whole crude oil (WCO), as well as the octane number that can be predicted for the naphtha fraction.

In steps 235, 240, 245, and 250, respectively, the properties of a cetane number, pour point, cloud point and aniline point for the gas oil (GO) fraction of the crude oil are calculated, in step 253 the aromaticity for the whole crude oil (WCO) is calculated, and in step 255 the property of an octane number for the naphtha fraction of the crude oil is calculated. While FIG. 2 shows the steps performed sequentially, they can be performed in parallel or in any order. In certain embodiments, only one or more steps 235, 240, 245, 250, 253, 255 are carried out. In these steps, the one or more indicative properties are determined as follows:

$$\text{Indicative property} = K + X1*DEN + X2*DEN^2 + X3*DEN^3 + X4*TGAI + X5*TGAI^2 + X6*TGAI^3 + X7*DEN*TGAI \quad (3);$$

where:

DEN=density of the crude oil sample; and

K, X1-X7, are constants for the properties to be predicted that are developed using linear regression analysis of hydrocarbon data from TGA.

Figure 3:
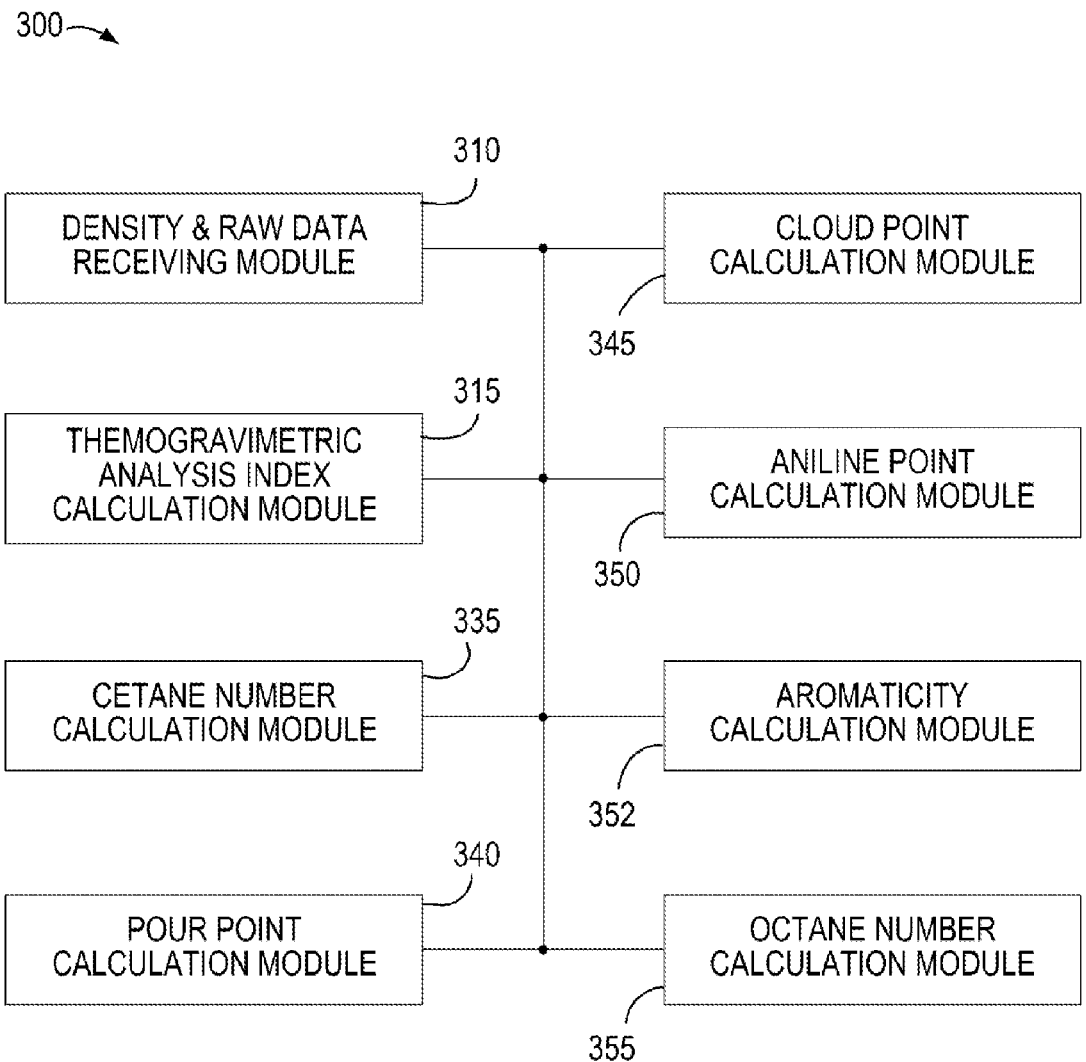
FIG. 3 is a schematic block diagram of modules of an embodiment of the invention.

FIG. 3 illustrates a schematic block diagram of modules in accordance with an embodiment of the present invention, system 300. Density and raw data receiving module 310 receives the density of a sample of crude oil and thermogravimetric analysis data derived from the crude oil.

Thermogravimetric analysis index calculation module calculates the thermogravimetric analysis index from the TGA data.

Cetane number calculation module 335 derives the cetane number for the gas oil fraction of the crude oil as a function of the thermogravimetric analysis index and density of the sample.

Pour point calculation module 340 derives the pour point for the gas oil fraction of the crude oil as a function of the thermogravimetric analysis index and density of the sample.

Cloud point calculation module 345 derives the cloud point for the gas oil fraction of the crude oil as a function of the thermogravimetric analysis index and density of the sample.

Aniline point calculation module 350 derives the aniline point for the gas oil fraction of the crude oil as a function of the thermogravimetric analysis index and density of the sample.

Aromaticity calculation module 352 derives the aromaticity for the whole crude oil as a function of the thermogravimetric analysis index and density of the sample.

Octane number calculation module 355 derives the octane number for the naphtha fraction of the crude oil as a function of the thermogravimetric analysis index and density of the sample.

Figure 4:
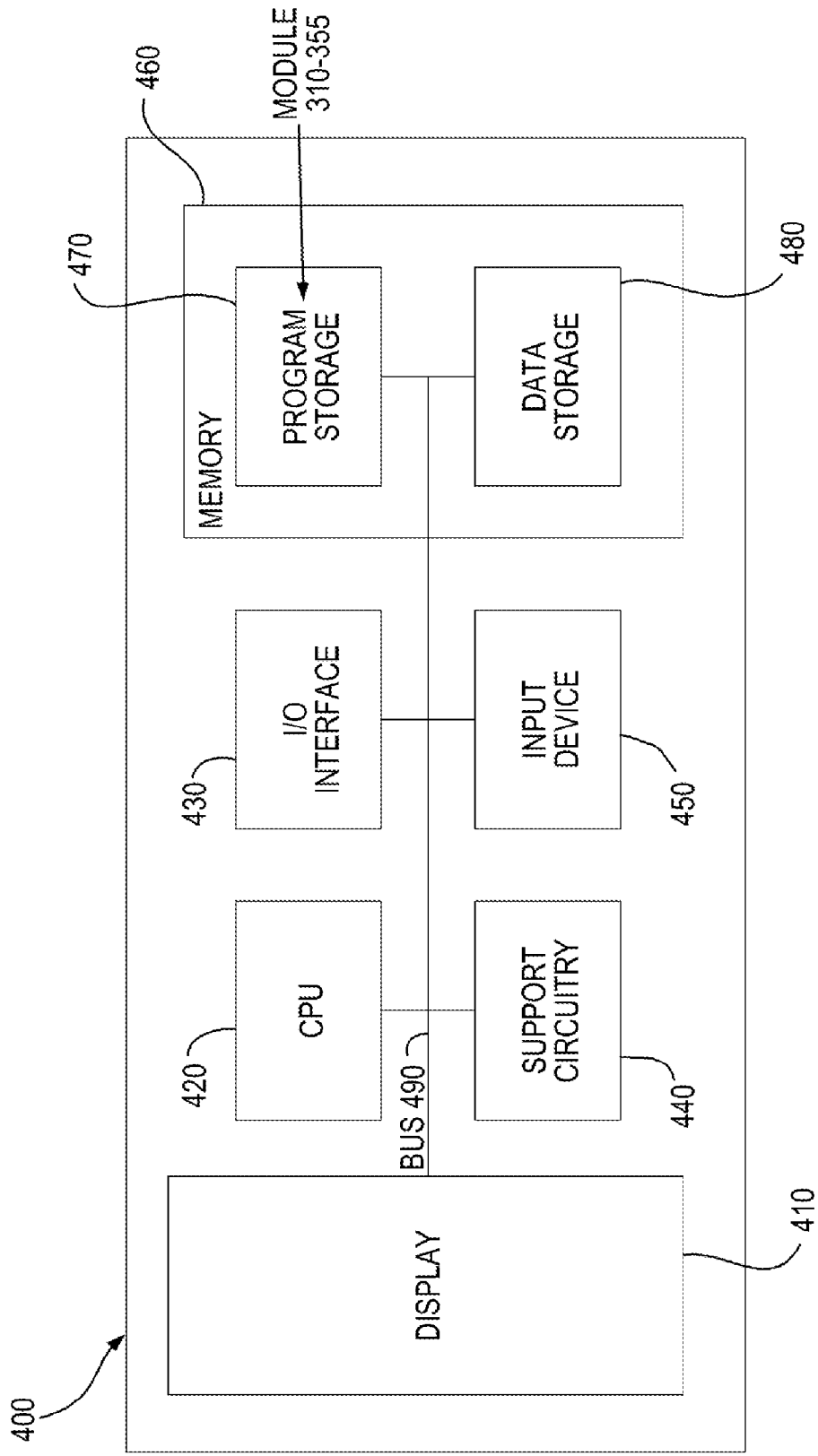
FIG. 4 is a block diagram of a computer system in which an embodiment of the invention is implemented.

FIG. 4 shows an exemplary block diagram of a computer system 400 in which the partial discharge classification system of the present invention can be implemented. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a density and raw data receiving module 310, thermogravimetric analysis index calculation module 315, cetane number calculation module 335, pour point calculation module 340, cloud point calculation module 345, aniline point calculation module 350, aromaticity calculation module 352, and octane number calculation module 355. Data storage memory 480 stores results and other data generated by the one or more modules of the present invention.

It is to be appreciated that the computer system 400 can be any computer such as a personal computer, minicomputer, workstation, mainframe, a dedicated controller such as a programmable logic controller, or a combination thereof. While the computer system 400 is shown, for illustration purposes, as a single computer unit, the system can comprise a group of computers which can be scaled depending on the processing load and database size.

Computer system 400 preferably supports an operating system, for example stored in program storage memory 470 and executed by the processor 420 from volatile memory. According to an embodiment of the invention, the operating system contains instructions for interfacing computer system 400 to the Internet and/or to private networks.

EXAMPLE 1

A set of constants K and X1-X7 was determined using linear regression for the indicative properties cetane number, pour point, cloud point, aniline point, octane number, and aromaticity. These constants were determined based on known actual distillation data for plural crude oil samples and their corresponding indicative properties. These constants are given in Table 3.

TABLE 3

| Constants | Cetane Number | Pour Point | Cloud Point | Aniline Point | Octane Number | WCO-AROM |
|---|---|---|---|---|---|---|
| K  |  3.4440824E+06 |  4.8586818E+06 |  2.9180642E+05 |  1.5741617E+06 | −3.1407161E+05 | −1.2131981E+05 |
| X1 | −1.1648748E+07 | −1.6445177E+07 | −9.9096539E+05 | −5.3253923E+06 |  1.1079386E+06 |  4.1952545E+05 |
| X2 |  1.2971167E+07 |  1.8314457E+07 |  1.1102599E+06 |  5.9279491E+06 | −1.2925048E+06 | −4.7011378E+05 |
| X3 | −4.7663268E+06 | −6.7294243E+06 | −4.1141986E+05 | −2.1769469E+06 |  5.0229227E+05 |  1.7360561E+05 |
| X4 |  3.4781476E+02 |  5.1784158E+02 |  2.4644626E+01 |  1.6833776E+02 | −2.1800822E+01 | −3.0649367E+01 |
| X5 | −3.0996298E−01 | −4.9994583E−01 | −2.4183985E−02 | −1.6081980E−01 |  6.9721231E−02 |  6.2885397E−02 |
| X6 |  3.1335567E−04 |  5.0732788E−04 |  2.4017172E−05 |  1.6443813E−04 | −7.3440477E−05 | −6.4167386E−05 |
| X7 | −2.8259387E+02 | −4.0725036E+02 | −1.9062052E+01 | −1.3337068E+02 |  0 |  1.1934777E+01 |

The following example is provided to demonstrate an application of equation (3). A sample of Arabian medium crude with a 15° C./4° C. density of 0.8828 Kg/l was analyzed by TGA, using the described method. The tabulated results follow in Table 4:

TABLE 4

| | API = 27.4° |
|---|---|
| W % | Temperature, ° C. |
| 0 | 21 |
| 1 | 23 |

TABLE 4-continued

| W % | API = 27.4° Temperature, °C. |
|---|---|
| 2 | 28 |
| 3 | 34 |
| 4 | 40 |
| 5 | 46 |
| 6 | 51 |
| 7 | 56 |
| 8 | 61 |
| 9 | 66 |
| 10 | 71 |
| 11 | 76 |
| 12 | 81 |
| 13 | 86 |
| 14 | 90 |
| 15 | 95 |
| 16 | 100 |
| 17 | 104 |
| 18 | 109 |
| 19 | 114 |
| 20 | 118 |
| 21 | 123 |
| 22 | 127 |
| 23 | 132 |
| 24 | 136 |
| 25 | 141 |
| 26 | 145 |
| 27 | 150 |
| 28 | 154 |
| 29 | 158 |
| 30 | 163 |
| 31 | 167 |
| 32 | 171 |
| 33 | 176 |
| 34 | 180 |
| 35 | 184 |
| 36 | 188 |
| 37 | 193 |
| 38 | 197 |
| 39 | 201 |
| 40 | 205 |
| 41 | 209 |
| 42 | 214 |
| 43 | 218 |
| 44 | 222 |
| 45 | 226 |
| 46 | 230 |
| 47 | 235 |
| 48 | 239 |
| 49 | 243 |
| 50 | 247 |
| 51 | 252 |
| 52 | 256 |
| 53 | 260 |
| 54 | 264 |
| 55 | 269 |
| 56 | 273 |
| 57 | 277 |
| 58 | 282 |
| 59 | 286 |
| 60 | 291 |
| 61 | 295 |
| 62 | 300 |
| 63 | 304 |
| 64 | 309 |
| 65 | 314 |
| 66 | 319 |
| 67 | 324 |
| 68 | 329 |
| 69 | 334 |
| 70 | 339 |
| 71 | 344 |
| 72 | 350 |
| 73 | 355 |
| 74 | 360 |
| 75 | 366 |
| 76 | 372 |
| 77 | 380 |
| 78 | 392 |
| 79 | 411 |
| 80 | 423 |
| 81 | 434 |
| 82 | 444 |
| 83 | 450 |
| 84 | 457 |
| 85 | 464 |
| 86 | 471 |
| 87 | 481 |
| 88 | 496 |
| 89 | 516 |
| 90 | 530 |
| 91 | 539 |
| 92 | 547 |
| 93 | 553 |
| 94 | 559 |
| 95 | 564 |
| 96 | 569 |
| 97 | 574 |
| 98 | 579 |
| 99 | 584 |
| 100 | 595 |

Applying equation (1), TGAI was calculated to be:

$$TGAI = \frac{\left[\begin{array}{l}5*T_5 + 10*T_{10} + 20*T_{20} + 30*T_{30} + 40*T_{40} + 50*\\T_{50} + 60*T_{60} + 70*T_{70} + 80*T_{80} + 90*T_{90} + 95*T_{95}\end{array}\right]}{[5 + 10 + 20 + 30 + 40 + 50 + 60 + 70 + 80 + 90 + 95]}$$

$$= [5*46 + 10*71 + 20*118 + 30*163 + 40*205 + 50*247 +$$

$$60*291 + 70*339 + 80*423 + 90*530 + 95*564]/$$

$$[5 + 10 + 20 + 30 + 40 + 50 + 60 + 70 + 80 + 90 + 95]$$

$$= 205,060/550$$

$$= 372.8363$$

The TGAI was therefore calculated to be 372.8363. Applying equation (3) and the constants from Table 3:

Cetane Number$_{GO}$(CET)=$K_{CET}$+$X1_{CET}$*DEN+ $X2_{CET}$*DEN$^2$+$X3_{CET}$*DEN$^3$+$X4_{CET}$*TGAI+ $X5_{CET}$*TGAI$^2$+$X6_{CET}$*TGAI$^3$+ $X7_{CET}$*DEN*TGAI=(3.4440824E+06)+ (−1.1648748E+07)(0.8828)+(1.2971167E+07) (0.8828)$^2$+(−4.7663268E+06)(0.8828)$^3$+ (3.4781476E+02)(372.8363)+(−3.0996298E−01) (372.8363)$^2$+(3.1335567E−04)(372.8363)$^3$+ (−2.8259387E+02)(0.8828)(372.8363)=59

Pour Point$_{GO}$(PP)=$K_{PP}$+$X1_{PP}$*DEN+$X2_{PP}$*DEN$^2$+ $X3_{PP}$*DEN$^3$+$X4_{PP}$*TGAI+$X5_{PP}$*TGAI$^2$+ $X6_{PP}$*TGAI$^3$+$X7_{PP}$*DEN*TGAI=(4.8586818E+ 06)+(−1.6445177E+07)(0.8828)+(1.8314457E+ 07)(0.8828)$^2$+(−6.7294243E+06)(0.8828)$^3$+ (5.1784158E+02)(372.8363)+(−4.9994583E−01) (372.8363)$^2$+(5.0732788E−04)(372.8363)$^3$+ (−4.0725036E+02)(0.8828)(372.8363)=−10

Cloud Point$_{GO}$(CP)=$K_{CP}$+$X1_{CP}$*DEN+$X2_{CP}$*DEN$^2$+ $X3_{CP}$*DEN$^3$+$X4_{CP}$*TGAI+$X5_{CP}$*TGAI$^2$+ $X6_{CP}$*TGAI$^3$+$X7_{CP}$*DEN*TGAI=(2.9180642E+ 05)+(−9.9096539E+05)(0.8828)+(1.1102599E+ 06)(0.8828)$^2$+(−4.1141986E+05)(0.8828)$^3$+ (2.4644626E+01)(372.8363)+(−2.4183985E−02) (372.8363)$^2$+(2.4017172E−05)(372.8363)$^3$+ (−1.9062052E+01)(0.8828)(372.8363)=−11

Aniline Point$_{GO}$(AP)=$K_{AP}$+$X1_{AP}$*DEN+$X2_{AP}$*DEN$^2$+ $X3_{AP}$*DEN$^3$+$X4_{AP}$*TGAI+$X5_{AP}$*TGAI$^2$+ $X6_{AP}$*TGAI$^3$+$X7_{AP}$*DEN*TGAI=(1.5741617E+ 06)+(−5.3253923E+06)(0.8828)+(5.9279491E+

$$06)(0.8828)^2+(-2.1769469E+06)(0.8828)^3+$$
$$(1.6833776E+02)(372.8363)+(-1.6081980E-01)$$
$$(372.8363)^2+(1.6443813E-04)(372.8363)^3+$$
$$(-1.3337068E+02)(0.8828)(372.8363)=66$$

$$Aromaticity_{WCO}(AROM)=K_{AROM}+X1_{AROM}*DEN+$$
$$X2_{AROM}*DEN^2+X3_{AROM}*DEN^3+$$
$$X4_{AROM}*TGAI+X5_{AROM}*TGAI^2+$$
$$X6_{AROM}*TGAI^3+X7_{AROM}*DEN*TGAI=$$
$$(-1.2131981E+05)+(4.1952545E+05)(0.8828)+$$
$$(-4.7011378E+05)(0.8828)^2+(1.7360561E+05)$$
$$(0.8828)^3+(-3.0649367E+01)(372.8363)+$$
$$(6.2885397E-02)(372.8363)^2+(-6.4167386E-$$
$$05)(372.8363)^3+(1.1934777E+01)(0.8828)$$
$$(372.8363)=18$$

$$Octane\ Number(ON)=K_{ON}+X1_{ON}*DEN+$$
$$X2_{ON}*DEN^2+X3_{ON}*DEN^3+X4_{ON}*TGAI+$$
$$X5_{ON}*TGAI^2+X6_{ON}*TGAI^3+X7_{ON}*DEN*TGAI=$$
$$(-3.1407161E+05)+(1.1079386E+06)(0.8828)+$$
$$(-1.2925048E+06)(0.8828)^2+(5.0229227E+05)$$
$$(0.8828)^3+(-2.1800822E+01)(372.8363)+$$
$$(6.9721231E-02)(372.8363)^2+(-7.3440477E-$$
$$05)(372.8363)^3+(0)(0.8828)(372.8363)=55$$

Accordingly, as shown in the above example, indicative properties including cetane number, pour point, cloud point, aniline point, and aromaticity can be assigned to the crude oil samples without fractionation/distillation (crude oil assays).

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to *In re Beauregard*, 35 U.S.P.Q.2d 1383 (U.S. Pat. No. 5,710,578), the present invention contemplates and includes this type of computer readable media within the scope of the invention. In certain embodiments, pursuant to *In re Nuijten*, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

We claim:

1. A system for evaluating a crude oil sample and calculates an indicative property of a gas oil or naphtha fraction of the crude oil sample without first distilling said gas oil or naphtha fraction, the system comprising:
    a thermogravimetric analyzer;
    a non-volatile memory device that stores calculation modules and data, the data including density of the crude oil sample and TGA data from an analysis of the crude oil sample as determined by the thermogravimetric analyzer;
    a processor coupled to the non-volatile memory;
    a first calculation module that retrieves the TGA data from the non-volatile memory device, calculates a crude oil thermogravimetric analysis index from a weighted mean of mass loss percentage versus heating temperature as indicated by the TGA data, and transfers the calculated crude oil thermogravimetric analysis index into the non-volatile memory; and
    a second calculation module that calculates the indicative property for the gas oil or naphtha fraction of the crude oil from a two-variable polynomial equation with predetermined constant coefficients developed using linear regression techniques, and that stores the indicative property into the non-volatile memory device;
    wherein the two variables of the two-variable polynomial equation are the crude oil thermogravimetric analysis index and the density of the crude oil sample.

2. The system of claim 1, wherein the indicative property is a cetane number.

3. The system of claim 1, wherein the indicative property is a pour point.

4. The system of claim 1, wherein the indicative property is a cloud point.

5. The system of claim 1, wherein the indicative property is an aniline point.

6. The system of claim 1, wherein the indicative property is an aromaticity.

7. The system of claim 1, wherein the indicative property is an octane number.

8. The system of claim 1, wherein a temperature range for the TGA analyzer is 20-1000° C.

9. The system of claim 1, wherein the heating rate is in a range of 0.1-100° C./minute.

10. The system of claim 1, wherein the thermogravimetric analysis index of the crude oil is calculated at a 50 W % point of the TGA data.

11. The system of claim 1, wherein the thermogravimetric analysis index of the crude oil is calculated by taking an average of temperature data.

12. The system of claim 1, wherein the thermogravimetric analysis index of the crude oil is calculated by taking a weighted average of temperature data.

13. The system of claim 1, wherein the thermogravimetric data is obtained directly from core and/or drill cuttings material.

14. A method for evaluating a crude oil sample to determine an indicative property of a gas oil or naphtha fraction of the crude oil sample without first distilling said gas oil or naphtha fraction, the method comprising:
    obtaining a density of the crude oil sample; subjecting said crude oil sample to a TGA analysis using a thermogravimetric analyzer; calculating a crude oil thermogravimetric analysis index for the crude oil sample from a weighted mean of mass loss percentage versus heating temperature as indicated by a TGA data; and calculating and recording the indicative property for the gas oil or naphtha fraction of the crude oil from a two-variable polynomial equation with predetermined constant coefficients developed using linear regression techniques; wherein the two variables of the two-variable polynomial equation are the crude oil thermogravimetric analysis index and the density of the crude oil sample.

15. The system of claim 14, wherein the indicative property is a cetane number.

16. The system of claim 14, wherein the indicative property is a pour point.

17. The system of claim 14, wherein the indicative property is a cloud point.

18. The system of claim 14, wherein the indicative property is an aniline point.

19. The system of claim 14, wherein the indicative property is an aromaticity.

20. The system of claim 14, wherein the indicative property is an octane number.

21. The system of claim 1, wherein a temperature range for the TGA analyzer is 20-1000° C.

22. The system of claim 14, wherein the heating rate is in a range of 0.1-100° C./minute.

23. The system of claim 14, wherein the thermogravimetric analysis index of the crude oil is calculated at a 50 W % point of the TGA data.

24. The system of claim 14, wherein the thermogravimetric analysis index of the crude oil is calculated by taking an average of temperature data.

25. The system of claim 14, wherein the thermogravimetric analysis index of the crude oil is calculated by taking a weighted average of temperature data.

26. The method of claim 14, wherein the thermogravimetric data is obtained directly from core and/or drill cuttings material.

* * * * *